United States Patent
Domanus et al.

(10) Patent No.: US 9,890,425 B2
(45) Date of Patent: Feb. 13, 2018

(54) SYSTEMS AND METHODS FOR DETECTION OF GENOMIC COPY NUMBER CHANGES

(71) Applicant: Abbott Molecular Inc., Des Plaines, IL (US)

(72) Inventors: Marc H. Domanus, Naperville, IL (US); Shiaolan Y. Ho, Wilmette, IL (US); Dae Hyun Kim, Northbrook, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 0 days.

(21) Appl. No.: 14/208,874

(22) Filed: Mar. 13, 2014

(65) Prior Publication Data

US 2014/0296094 A1 Oct. 2, 2014

Related U.S. Application Data

(60) Provisional application No. 61/787,419, filed on Mar. 15, 2013.

(51) Int. Cl.
*C12Q 1/68* (2006.01)

(52) U.S. Cl.
CPC ........... *C12Q 1/6874* (2013.01); *C12Q 1/686* (2013.01); *C12Q 1/6858* (2013.01); *C12Q 1/6886* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,130,238 A | 7/1992 | Malek et al. |
| 5,270,184 A | 12/1993 | Walker et al. |
| 5,283,174 A | 2/1994 | Arnold, Jr. et al. |
| 5,399,491 A | 3/1995 | Kacian et al. |
| 5,455,166 A | 10/1995 | Walker |
| 5,480,784 A | 1/1996 | Kacian et al. |
| 5,641,658 A | 6/1997 | Adams et al. |
| 5,695,934 A | 12/1997 | Brenner |
| 5,714,330 A | 2/1998 | Brenner et al. |
| 5,750,341 A | 5/1998 | Macevicz |
| 5,824,518 A | 10/1998 | Kacian et al. |
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,329,492 B2 | 2/2008 | Hardin et al. |
| 7,482,120 B2 | 1/2009 | Buzby et al. |
| 7,501,245 B2 | 3/2009 | Quake et al. |
| 7,668,697 B2 | 2/2010 | Volkov et al. |
| 7,718,369 B2 | 5/2010 | Tomlins et al. |
| 7,790,418 B2 | 9/2010 | Mayer |
| 7,972,820 B2 | 7/2011 | Mayer |
| 8,765,382 B2 | 7/2014 | Drmanac |
| 2003/0099956 A1* | 5/2003 | Ward et al. ........................ 435/6 |
| 2004/0197791 A1* | 10/2004 | Makarov et al. ................. 435/6 |
| 2005/0130173 A1 | 6/2005 | Leamon et al. |
| 2006/0046265 A1 | 3/2006 | Becker et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |
| 2011/0028336 A1 | 2/2011 | Chinnaiyan et al. |
| 2011/0118145 A1 | 5/2011 | Akmaev et al. |
| 2012/0015839 A1 | 1/2012 | Chinnaiyan |

(Continued)

FOREIGN PATENT DOCUMENTS

| | | |
|---|---|---|
| EP | 0684315 A1 | 11/1995 |
| WO | WO-0018957 A1 | 4/2000 |

(Continued)

OTHER PUBLICATIONS

Mardis, Annu. Rev. Genom. Hum. Genet. 9:387-402, 2008.*
Adessi C., et al., "Solid Phase DNA Amplification: Characterisation of Primer Attachment and Amplification Mechanisms," Nucleic Acids Research, 2000, vol. 28 (20), p. E87.
Aitman T.J., et al., "Copy Number Polymorphism in Fcgr3 Predisposes to Glomerulonephritis in Rats and Humans," Nature, 2006, vol. 439 (7078), pp. 851-855.
Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.
Bennett S.T., et al., "Toward the 1,000 Dollars Human Genome," Pharmacogenomics, 2005, vol. 6 (4), pp. 373-382.
Birren B., et al., eds., Genome Analysis—A Laboratory Manual, vol. 1, Cold Spring Harbor Laboratory Press, 1997, Table of Contents.

(Continued)

*Primary Examiner* — Nancy Treptow
(74) *Attorney, Agent, or Firm* — David A. Casimir; Casimir Jones, S.C.

(57) ABSTRACT

The present invention relates to systems and methods for detecting genomic copy number changes. In particular, the present invention relates to next generation sequencing methods for detection of copy number changes.

12 Claims, 9 Drawing Sheets

(56) References Cited

U.S. PATENT DOCUMENTS

| | | | |
|---|---|---|---|
| 2013/0059738 A1 | 3/2013 | Leamon et al. | |
| 2013/0261196 A1* | 10/2013 | Diamond et al. | 514/789 |

FOREIGN PATENT DOCUMENTS

| | | |
|---|---|---|
| WO | WO-2006084132 A2 | 8/2006 |
| WO | 2011090559 A1 | 7/2011 |
| WO | 2012051346 A1 | 4/2012 |

OTHER PUBLICATIONS

Brenner S., et al., "Gene Expression Analysis by Massively Parallel Signature Sequencing (MPSS) on Microbead Arrays," Nature Biotechnology, 2000, vol. 18 (6), pp. 630-634.

Cappuzzo F., et al., "Epidermal Growth Factor Receptor Gene and Protein and Gefitinib Sensitivity in Non-Small-Cell Lung Cancer," Journal of the National Cancer Institute, 2005, vol. 97 (9), pp. 643-655.

Castle J.C., et al., "DNA Copy Number, Including Telomeres and Mitochondria, Assayed using Next-Generation Sequencing," BMC Genomics, 2010, vol. 11:244, 11 pages.

Conway C., et al., "Next-Generation Sequencing for Simultaneous Determination of Human Papillomavirus Load, Subtype, and Associated Genomic Copy Number Changes in Tumors," The Journal of Molecular Diagnostics, 2012, vol. 14 (2), pp. 104-111.

Cook E.H. Jr., et al., "Copy-Number Variations Associated with Neuropsychiatric Conditions," Nature, 2008, vol. 455 (7215), pp. 919-923.

Dressman D., et al., "Transforming Single Dna Molecules into Fluorescent Magnetic Particles for Detection and Enumeration of Genetic Variations," Proceedings of the National Academy of Sciences of the United States of America, 2003, vol. 100 (15), pp. 8817-8822.

Gai X., et al., "Rare Structural Variation of Synapse and Neurotransmission Genes in Autism," Molecular Psychiatry, 2012, vol. 17 (4), pp. 402-411.

Gonzalez E., et al., "The Influence of CCL3L1 Gene-Containing Segmental Duplications on HIV-1/AIDS Susceptibility," Science, 2005, vol. 307 (5714), pp. 1434-1440.

Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.

Iafrate A.J., et al., "Detection of Large-Scale Variation in the Human Genome," Nature Genetics, 2004, vol. 36 (9), pp. 949-951.

Knight S.J., et al., "Subtle Chromosomal Rearrangements in Children with Unexplained Mental Retardation," Lancet, 1999, vol. 354 (9191), pp. 1676-1681.

Kwoh D.Y., et al., "Transcription-Based Amplification System and Detection of Amplified Human Immunodeficiency Viru: Type 1 with a Bead-Based Sandwixh Hybridization Format," Proceeding of the National Academy of Sciences of the USA, 1989, vol. 86 (4), pp. 1173-1177.

Leamon J.H., et al., "A Massively Parallel Picotiterplate Based Platform for Discrete Picoliter-scale Polymerase Chain Reactions," Electrophoresis, 2003, vol. 24 (21), pp. 3769-3777.

Lizardi P.M., et al., "Exponential Amplification of Recombinant-RNA Hybridization Probes," Bio/Technology, 1988, vol. 6, pp. 1197-1202.

Lizardi P.M., et al., "Mutation Detection and Single-molecule Counting using Isothermal Rolling-circle Amplification," Nature Genetics, 1998, vol. 19 (3), pp. 225-232.

Lupski J.R., "Genomic Rearrangements and Sporadic Disease," Nature Genetics, 2007, vol. 39 (7 Suppl), pp. S43-S47.

MacLean D., et al., "Application of 'next-generation' Sequencing Technologies to Microbial Genetics," Nature Reviews Microbiology, 2009, vol. 7 (4), pp. 287-296.

Margulies M., et al., "Genome Sequencing in Microfabricated High-Density Picolitre Reactors," Nature, 2005, vol. 437 (7057), pp. 376-380.

Marioni J.C., et al., "Breaking the Waves: Improved Detection of Copy Number Variation from Microarray-Based Comparative Genomic Hybridization," Genome Biology, 2007, vol. 8 (10), R228.

Mitra R.D., et al., "Fluorescent in Situ Sequencing on Polymerase Colonies," Analytical Biochemistry, 2003, vol. 320 (1), pp. 55-65.

Mitra R.D., et al., "In Situ Localized Amplification and Contact Replication of Many Individual DNA Molecules," Nucleic Acids Research, 1999, vol. 27 (24), pp. e34.

Morozova O., et al., "Applications of Next-generation Sequencing Technologies in Functional Genomics," Genomics, 2008, vol. 92 (5), pp. 255-264.

Mullis K.B., et al., "Specific Synthesis of Dna In Vitro Via a Polymerase-catalyzed Chain Reaction," Methods in Enzymology, 1987, vol. 155, pp. 335-350.

Murakawa G.J., et al., "Direct Detection of HIV-1 RNA from AIDS and ARC Patient Samples," DNA: A Journal of Molecular Biology, 1988, vol. 7 (4), pp. 287-295.

Nelson N. C., et al., "Detection of Acridinium Esters by Chemiluminescence," in: Nonisotopic Probing, Blotting and Sequencing, 1995, Chapter 17, Academic Press, Inc., pp. 391-428.

Pennisi E., "Genomics. Semiconductors Inspire New Sequencing Technologies," Science, 2010, vol. 327 (5970), p. 1190.

Perler F.B., et al., "Thermostable Dna Polymerases," Advances in Protein Chemistry, 1996, vol. 48, pp. 377-435.

Persing, "In Vitro Nucleic Acid Amplification Techniques," Diagnostic Molecular Microbiology, 1993, pp. 51-77.

Pinto D., et al., "Functional impact of global rare copy number variation in autism spectrum disorders," Nature, 2010, vol. 466 (7304), pp. 368-372.

Redon R., et al., "Global Variation in Copy Number in the Human Genome," Nature, 2006, vol. 444 (7118), pp. 444-454.

Ropers H.H., "New Perspectives for the Elucidation of Genetic Disorders," American Journal of Human Genetics, 2007, vol. 81 (2), pp. 199-207.

Sebat J., et al., "Large-Scale Copy Number Polymorphism in the Human Genome," Science, 2004, vol. 305 (5683), pp. 525-528.

Sebat J., et al., "Strong Association of de Novo Copy Number Mutations with Autism," Science, 2007, vol. 316 (5823), pp. 445-449.

Shendure J., et al., "Accurate Multiplex Polony Sequencing of an Evolved Bacterial Genome," Science, 2005, vol. 309 (5741), pp. 1728-1732.

St Clair D., "Copy Number Variation and Schizophrenia," Schizophrenia Bulletin, 2009, vol. 35 (1), pp. 9-12.

Thum O., et al., "Functionalized DNA: A New Replicable Biopolymer We Thank Dr. andreas Marx, University of Bonn, for Helpful Advice and Discussions. This Work was Supported by the Fonds Der Chemischen Industrie, the Karl-Ziegler Stiftung, and the Deutsche Forschungsgemeinschaft," Angewandte Chemie, 2001, vol. 40 (21), pp. 3990-3993.

Voelkerding K.V., et al., "Next-Generation Sequencing: from Basic Research to Diagnostics," Clinical Chemistry, 2009, vol. 55 (4), pp. 641-658.

Walker G.T., et al., "Isothermal in Vitro Amplification of DNA by a Restriction Enzyme/DNA Polymerase System," Proceedings of the National Academy of Sciences, 1992, vol. 89 (1) pp. 392-396.

Weiss R., "Hot Prospect for New Gene Amplifier," Science, 1991, vol. 254 (5036), pp. 1292-1293.

Wong K.K., et al., "A Comprehensive Analysis of Common Copy-Number Variations in the Human Genome," American Journal of Human Genetics, 2007, vol. 80 (1), pp. 91-104.

Wood H.M., et al., "Using Next-Generation Sequencing for High Resolution Multiplex Analysis of Copy Number Variation from Nanogram Quantities of DNA from Formalin-Fixed Paraffin-Embedded Specimens," Nucleic Acids Research, 2010, vol. 38 (14), e151.

Xi R., et al., "Copy Number Variation Detection in Whole-Genome Sequencing Data Using the Bayesian Information Criterion," Proceedings of the National Academy of Sciences, 2011, vol. 108 (46), pp. E1128-E1136.

(56) References Cited

OTHER PUBLICATIONS

Zong C., et al., "Genome-Wide Detection of Single-Nucleotide and Copy-Number Variations of a Single Human Cell," Science, 2012, vol. 338 (6114), pp. 1622-1626.
Supplementary European search report for Application No. EP14767590, dated Nov. 8, 2016, 9 pages.
International Search Report for Application No. PCT/US2014/025883, dated Mar. 27, 2015, 5 pages.
Zhang C., et al.,"A Single Cell Level Based Method for Copy Number Variation Analysis by Low Coverage Massively Parallel Sequencing," Public Library of Science One, 2013, vol. 8 (1), pp. 1-9.

* cited by examiner

FIG. 1

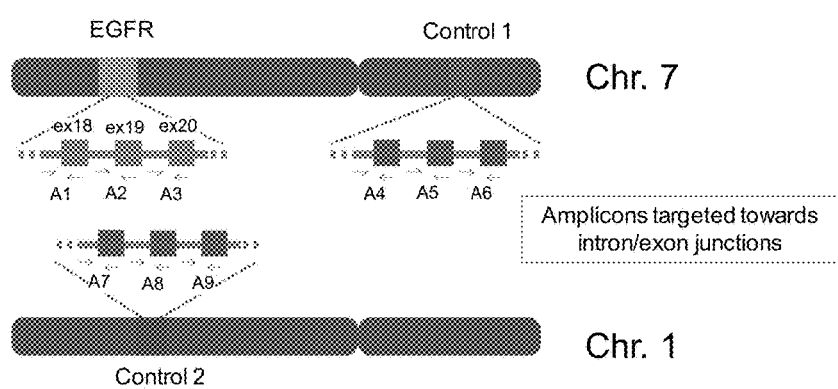

- Low-cycle PCR during NGS amplicon library generation to maintain copy number representation
- Utilize number of sequence reads (total counts for EGFR, controls 1 & 2) to quantify relative copy number of EGFR
  - Use the median of the three amplicons' read count
  - Read ratio between EGFR (E), Control 1 (C1) and Control 2 (C2) will determine whether wild-type, polysomy, or locus specific amplification (allele specific)

FIG. 2

NGS Based CNV Detection - Feasibility Design

FFPE Glioblastoma Samples
Non-amplified sample: 1167356B
Amplified Sample: 1167348B

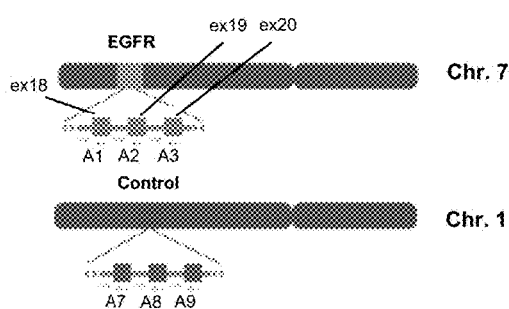

NGS output

| | |
|---|---|
| ...gtcatgcgtccgagcctgtgggg... | SEQ ID NO.: 1 |
| ...gtaatgcgtccgagcctgtgggg... | SEQ ID NO.: 2 |
| ...gtaattatgtggtgacagatcacggc... | SEQ ID NO.: 3 |
| ...gtcattatgtggtgacagatcacggc... | SEQ ID NO.: 4 |
| ...gtcattatgtggtgacagatcacggc... | SEQ ID NO.: 4 |
| ...gtcattatgtggtgacagatcacggc... | SEQ ID NO.: 4 |
| ...gtcattatgtggtgacagatcacggc... | SEQ ID NO.: 4 |
| ...gtcattatgtggtgacagatcacggc... | SEQ ID NO.: 4 |
| ...gtcattatgtggtgacagatcacggc... | SEQ ID NO.: 4 |
| ...gtaattatgtggtgacagatcacggc... | SEQ ID NO.: 3 |
| ...gtcattatgtggtgacagatcacggc... | SEQ ID NO.: 4 |
| ...gtcattatgtggtgacagatcacggc... | SEQ ID NO.: 4 |

- Utilize number of sequence reads (total counts for EGFR and control) to quantify relative copy number of EGFR
- Sequence read count ratio between EGFR and control(s) can determine whether wild-type (non-amplified), polysomy, or locus specific amplification (allele specific)

- C1 = Amplicon on Chr1; C2 = Amplicon on Chr7 (e.g. housekeeping gene) (same as Chr EGFR)

SYSTEMS AND METHODS FOR DETECTION OF GENOMIC COPY NUMBER CHANGES

This application claims priority to Provisional Patent Application Ser. No. 61/787,419, filed Mar. 15, 2013, which is herein incorporated by reference in its entirety.

FIELD OF INVENTION

The present invention relates to systems and methods for detecting genomic copy number changes. In particular, the present invention relates to next generation sequencing methods for detection of copy number changes.

BACKGROUND

Copy number variations (CNVs) are the gains or losses of genomic regions which range from 500 bases on upwards in size (often between five thousand and five million bases). Whole genome studies have revealed the presence of large numbers of CNV regions in human and a broad range of genetic diversity among the general population. CNVs have been the focus of many recent studies because of their roles in human genetic disorders. See, for example Iafrate et al., 2004, Nat Genet 36: 949-951; Sebat et al., 2004, Science 305: 525-528; Redon et al., 2006, Nature 444: 444-454; Wong et al., 2007, Am J Hum Genet 80: 91-104; Ropers, 2007, Am J Hum Genet 81: 199-207; Lupski, 2007, Nat Genet 39: S43-S47, each of which is incorporated by reference. Aneuploidy, such as trisomy or whole chromosome deletion, is a limiting type of copy number variation associated with a variety of human diseases.

Comparative genomic hybridization (CGH) is one technique used to detect copy number changes and other genomic aberrations. In CGH, a test sample is typically compared to a reference sample to determine the existence of genomic aberrations. Typically, nucleic acids from the test sample are differentially labeled from nucleic acids from the reference sample, and nucleic acids from both samples are typically hybridized to a microarray of probes. Signals are then detected from nucleic acids hybridized to the microarray. Deviations of the log ratio of the signals generated from the labels of the test and reference nucleic acids from an expected value (e.g., zero for diploid regions) are detected and may be used as an indication of copy number differences.

The currently available CGH techniques still have noteworthy limitations. For example, certain genome-wide artifacts commonly known as "GC waves" (which may be due to the guanine/cytosine (GC) content of the probes used in CGH) can cause the log ratio to deviate from its expected value resulting in false positives. GC-waves can add large scale variability to the probe signal ratios and interfere with data analysis algorithms as they can skew signal logarithmic ratio data away from expected values. The GC-wave artifact can increase the potential for false positive aberration calls in specific genomic regions, and can also obscure true aberration calls (See Marioni et al., (2007), Genome Biology, 8:R228).

Fluorescent in-situ hybridization (FISH), realtime PCR, and digital PCR (ddPCR) methods have been used to detect gene copy number changes, however the degree to which one can multiplex (samples, regions of interest, and variant types) is limited using these technologies. Next generation sequencing has the ability to perform a significantly higher degree of multiplexing (sample multiplexing, targeted region multiplexing, and variant type multiplexing all in a single assay) compared to FISH, real time PCR, and digital PCR technologies (See e.g., (Castle et al., (2010) BMC Genomics, 11:244; Wood et al., Nucleic Acids Research, Vol. 38, No. 14, e151; Conway et al., (2012) The Journal of Molecular Diagnostics, Vol. 14, No. 2, p 104-111).

Furthermore, FISH in particular, lacks the 'fine' resolution to distinguish closely residing local variations. Sequencing methods such as whole genome sequencing have been used to detect copy number variations (Xi et al., PNAS 108: E1128 (2011); Zong et al., Science (2012) Vol. 338 no. 6114 pp. 1622-1626). However, such methods are time consuming, expensive, and require extensive bioinformatics analysis to determine copy number variations.

Additional methods for detecting CNVs are needed.

SUMMARY

The present invention relates to systems and methods for detecting genomic copy number changes. In particular, the present invention relates to next generation sequencing methods for detection of copy number changes.

For example, in some embodiments, the present invention provides a method of determining chromosomal copy number change (e.g., increase or decrease (e.g., deletion)) or gene expression change (e.g., increase or decrease) of a nucleic acid region of interest, comprising: a) amplifying nucleic acid from the region of interest and at least one control region to generate target and control amplicons; b) sequencing the target and control amplicons to generate sequencing reads; and c) comparing the level of target amplicon to the level of control amplicon. In some embodiments, 2 or more amplicons are generated from the target nucleic acid (e.g., 2, 3, 4, 5, 6, 7, 8, 9, 10 or more). In some embodiments, regions of interest are regions of nucleic acid less than an entire genome (e.g., chromosomes, arms of chromosomes, regions of chromosomes, one or more genes, or non-coding areas). In some embodiments, at least one control region comprises a first control region on the same chromosome as the region of interest and a second control region on a nucleic acid (e.g., chromosome) different from the region of interest. In some embodiments, the comparing comprises comparing the ratio of the first control amplicon to the second control amplicon, to the ratio of target amplicon to the second control amplicon. In some embodiments, a ratio of target amplicon to second control amplicon that is greater or lesser than the ratio of first control amplicon to the second control amplicon is indicative of chromosomal copy number change or gene expression change of the region of interest. In some embodiments, copy number change is at least 2 fold (e.g., at least 5, 10, 20, 30, 40 or more fold). In some embodiments, chromosomal copy number change or gene expression change of the region of interest is indicative of a diagnosis or prognosis of a disease (e.g., cancer) in a subject. In some embodiments, the prognosis is likelihood of the disease to progress, response of the disease to a treatment, or likelihood of the disease recurring. In some embodiments, the method further comprises determining a treatment course of action based on the diagnosis or prognosis. In some embodiments, the region of interest is genomic DNA and the chromosomal copy number change is an increase or decrease (e.g., deletion) of a gene located in the genomic DNA. In some embodiments, the region of interest is mRNA and the gene expression change is increased or decreased mRNA expression (e.g., due to a gene fusion). In some embodiments, the method further comprises the addition of nucleic acid adaptors to the amplicons during or after amplification. In some embodiments, adaptors are ligated after amplification or added during amplification (e.g., as a section of an amplification primer). In some embodiments, the sequencing is next generation sequencing. In some embodiments, 45 or less (e.g., 40, 35, 34, 33, 32, 31, 30, 29, 28, 27, 26, 25, 24, 23, 22, 20, 15, 10 or fewer) cycles of amplification are performed. The present invention is not limited to a particular type of primer. Examples include, but are not limited to, chemically modified primers, fluorescence-modified primers, functional primers (fusion primers), sequence specific primers, random primers, primers that have both specific and random sequences, and DNA and RNA primers.

In further embodiments, the present invention provides a method of determining chromosomal copy number change (e.g., increase or decrease) or gene expression change of a nucleic acid region of interest, comprising: a) amplifying nucleic acid from the region of interest and first and second control regions to generate target and control amplicons; b) sequencing the target and control amplicons to generate sequencing reads; and c) comparing the level of target amplicon to the level of control amplicon.

In additional embodiments, the present invention provides a method of determining chromosomal copy number change (e.g., increase or decrease) or gene expression change of a nucleic acid region of interest, comprising: a) amplifying nucleic acid from the region of interest and first and second control regions to generate target and first and second control amplicons; b) sequencing the target and control amplicons to generate sequencing reads; and c) comparing the ratio of the first control amplicon to the second control amplicon to the ratio of target amplicon to the second control amplicon.

In yet other embodiments, the present invention provides a method of determining chromosomal copy number change (e.g., increase or decrease) or gene expression change of a nucleic acid region of interest, comprising: a) amplifying nucleic acid from the region of interest and at least one control region to generate target and control amplicons, wherein the amplifying utilizes adaptor nucleic acids; b) sequencing the target and control amplicons to generate sequencing reads; and c) comparing the level of target amplicon to the level of control amplicon.

In additional embodiments, the present invention a method of determining chromosomal copy number change (e.g., increase or decrease) or gene expression change of a nucleic acid region of interest, comprising: a) amplifying nucleic acid from the region of interest and first and second control regions to generate target and first and second control amplicons; b) sequencing the target and control amplicons to generate sequencing reads; and c) comparing the ratio of the first control amplicon to the second control amplicon to the ratio of target amplicon to the second control amplicon; and d) determining copy number changes or altered expression of the region of interest when a ratio of target amplicon to second control amplicon that is greater or lesser than the ratio of first control amplicon to the second control amplicon is detected.

The present invention also provides a kit, comprising, consisting essentially of, or consisting of one or more or all of: a) a first set of primer pairs for amplification of a target nucleic acid; b) at least one second set of primers for amplification of a control nucleic acid; c) a plurality of nucleic acid adaptors; and optionally d) at least one sequencing primer that specifically hybridizes to the nucleic acid adaptors. In some embodiments, at least one set of second primers comprises two sets of primers for amplification of two control nucleic acids (e.g., a first control on the same chromosome as the target nucleic acid and a second control on a different nucleic acid (e.g., a different chromosome)). In some embodiments, the first set of primers specifically hybridizes to a gene of interest. In some embodiments, kits further comprise data analysis software.

Embodiments of the present invention provide a method of sequencing target amplicons and control amplicons, comprising: a) amplifying a library of target and control amplicons from target and control nucleic acid regions; and b) sequencing the library of amplicons using a massively parallel sequencing technique to generate a plurality of sequencing reads. In some embodiments, the method further comprises the step of detecting variations in copy number or expression of the target nucleic acid region when an increased number of sequencing reads are generated from the target region relative to the control regions.

The present invention further provides a kit, comprising, consisting essentially of, or consisting of one or more or all of: a) at least one first set of primer pairs for amplification of a target nucleic acid; b) at least two sets of primers for amplification of first and second control nucleic acids; c) a plurality of nucleic acid adaptors; and d) at least one sequencing primer that specifically hybridizes to the nucleic acid adaptors.

The present invention further provides a kit, comprising, consisting essentially of, or consisting of one or more or all of: a) at least one first set of primer pairs for amplification of a target nucleic acid; b) at least two sets of primers for amplification of first and second control nucleic acids, wherein the first control nucleic acid is on the same chromosome as the target and the second control is on a different nucleic acid than the control (e.g., a different chromosome); c) a plurality of nucleic acid adaptors; and d) at least one sequencing primer that specifically hybridizes to the nucleic acid adaptors.

The present invention additionally provides a composition comprising, consisting essentially of, or consisting of, a reaction mixture comprising a target nucleic acid; at least one first set of primer pairs for amplification of a target nucleic acid; at least one second set of primers for amplification of a control nucleic acid; a plurality of nucleic acid adaptors; and at least one sequencing primer that specifically hybridizes to the nucleic acid adaptors.

Additional embodiments will be apparent to persons skilled in the relevant art based on the teachings contained herein.

BRIEF DESCRIPTION OF THE DRAWINGS

FIG. 1 shows an exemplary assay design for CNV detection assays of embodiments of the present invention.

FIG. 2 shows an exemplary assay design for CNV detection assays of embodiments of the present invention.

DETAILED DESCRIPTION

Figure 3:
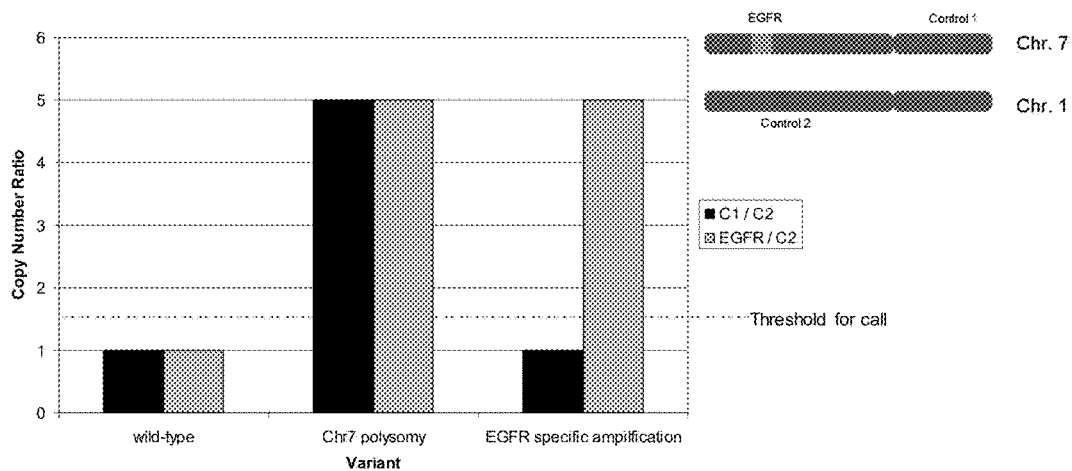
FIG. 3 shows theoretical results for EGFR copy number amplification.
Figure 4:
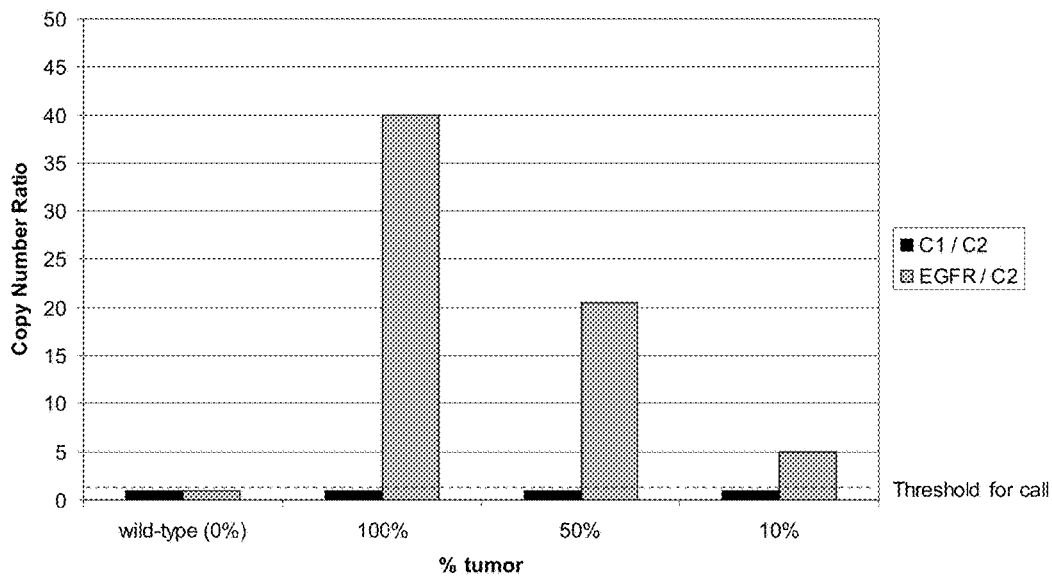
FIG. 4 shows theoretical results for EGFR copy number amplification of 40 with samples containing different amounts of tumor cells.
Figure 5:
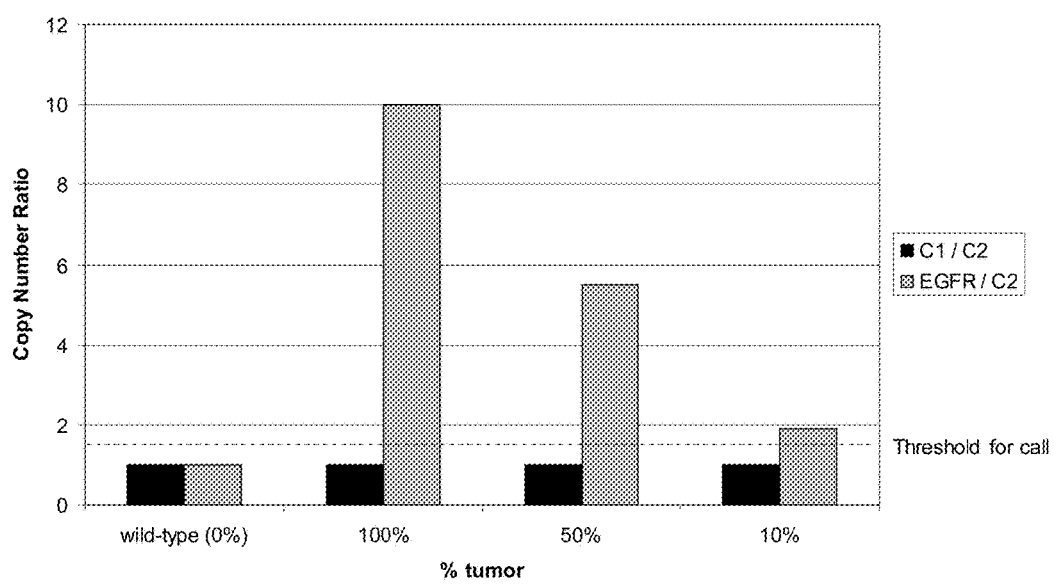
FIG. 5 shows theoretical results for EGFR copy number amplification of 10 with samples containing different amounts of tumor cells.
Figure 6:
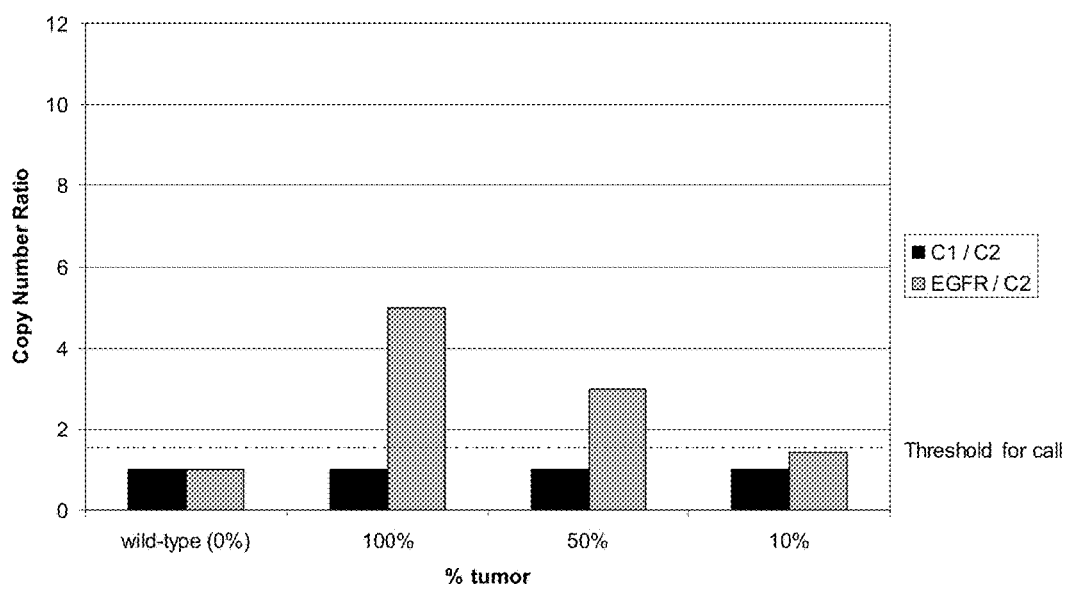
FIG. 6 shows theoretical results for EGFR copy number amplification of 5 with samples containing different amounts of tumor cells.

The present invention relates to systems and methods for detecting genomic copy number changes. In particular, the present invention relates to next generation sequencing methods for detection of copy number changes.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

The term "label" as used herein refers to any atom or molecule that can be used to provide a detectable (preferably quantifiable) effect, and that can be attached to a nucleic acid or protein. Labels include but are not limited to dyes; radiolabels such as $^{32}$P; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable. In some embodiments, nucleic acids are detected directly without a label (e.g., directly reading a sequence).

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method. In some embodiments, primers comprise additional sequences that do not hybridize to the nucleic acid of interest. For example, in some embodiments, primer contains an anchor sequence for use in a sequencing assay. The term "primer" includes chemically modified primers, fluorescence-modified primers, functional primers (fusion primers), sequence specific primers, random primers, primers that have both specific and random sequences, and DNA and RNA primers The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the terms "subject" and "patient" refer to any animal, such as a dog, a cat, a bird, livestock, and particularly a mammal, and preferably a human.

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "amplicon" refers to a nucleic acid generated via amplification reaction. The amplicon is typically double stranded DNA; however, it may be RNA and/or DNA:RNA. The amplicon comprises DNA complementary to a sample nucleic acid. In some embodiments, primer pairs are configured to generate amplicons from a sample nucleic acid. As such, the base composition of any given amplicon may include the primer pair, the complement of the primer pair, and the region of a sample nucleic acid that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used for subsequent analysis (e.g. base composition determination, for example, via direct sequencing). In some embodiments, the amplicon further comprises a length that is compatible with subsequent analysis.

As used herein, the term "library" refers to a plurality of nucleic acids. For example, in some embodiments, the present disclosure utilizes a library of amplicons. In some embodiments, libraries comprise 2 or more (e.g., 3 or more 5 or more, 7 or more, 9 or more, 10 or more, 20 or more, 30 or more, or 50 or more) nucleic acids (e.g., amplicons).

The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR), rolling circle amplification (RCA), or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "anchor" refers to a nucleic acid that serves as a template for annealing of a second nucleic acid. In some embodiments, anchors serve as annealing sites for sequencing primers (e.g., in next generation sequencing methods).

As used herein, the term "region of interest" refers to a nucleic acid that is analyzed (e.g., using one of the compositions, systems, or methods described herein). In some embodiments, the region of interest is a portion of a genome or region of genomic DNA (e.g., comprising one or chromosomes or one or more genes). In some embodiments, mRNA expressed from a region of interest is analyzed. In some embodiments, the copy number of a region of interest or the level of mRNA expressed from a region of interest is altered (e.g., increased, decreased, or deleted) relative to the level of a control region. In some embodiments, the altered copy number or level of expression is indicative of the presence or risk of a disease in a subject comprising the nucleic acid.

As used herein, the term "at least one control region" refers to a region distinct from the region of interest. In some embodiments, "at least one control region" refers to regions of a known genomic copy number of known level of expression. For example, in some embodiments, control regions are on the same or different nucleic acid molecules (e.g., chromosomes) than the region of interest.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. In some embodiments, samples comprise cells (e.g., tumor cells) or tissues (e.g., tumor or biopsy tissues) or nucleic acids (e.g., DNA or RNA) isolated from such cells or tissues. Environmental samples include environmental material such as surface matter, soil, mud, sludge, biofilms, water, and industrial samples. Such examples are not however to be construed as limiting the sample types applicable to the present invention.

Embodiments of the Technology

Although the disclosure herein refers to certain illustrated embodiments, it is to be understood that these embodiments are presented by way of example and not by way of limitation.

Copy number variation detection work to date in the next generation sequencing research community has been focused on CNV discovery but not on the development of assays capable of detecting copy number changes in targeted clinically relevant genomic regions. Embodiments of the present disclosure describe an amplicon based method to detect copy number variations in targeted regions of interest from human genomic samples. The percentage of next generation sequencing run 'real estate' occupied by such a targeted region of interest approach allows for a much higher degree of multiplexing per next generation sequencing run.

When looking at just a few regions of interest for copy number variation, the method described herein provide relevant information/data of those regions in limited amount due to the data having smaller/diluted coverage in those regions. This describes the time and cost of analysis compared to whole genome type analysis methods.

The methods disclosed here, based on amplicon based library generation for input to NGS, allows CNV detection of only the designated regions of interest within the whole genome. The regions of interest are specifically amplified by PCR along with control regions (where copy numbers are known/determined and not prone to variation), to provide a precise determination of relative copy number differences. In this way, the majority of the output data is relevant, thus enabling precise calculation (due to significant increase in data coverage) of copy number variation of the regions of interest. Also, sample multiplexing opportunities are more readily available due to each amplicon (ROI) only taking a small fraction of 'space' in the NGS input compared to whole genome.

Accordingly, embodiments of the present disclosure provide next generation sequencing assays and/or highly multiplexed assays (e.g., assays that detect 2 or more, 3 or more, 5 or more, 7 or more, 10 or more, 50 or more, 100 or more, 500 or more, or 1000 or more targets in a multiplex assay) capable of detecting targeted gene copy number changes in multiple targeted genomic regions simultaneously. In some embodiments, regions of interests (ROI) are first prepared using PCR (e.g., amplicon generation). In some embodiments, one or more amplicons per region of interest are generated (e.g., 2, 3, 4, 5 or more).

In some embodiments, limited amount of PCR cycles are used to maintain copy number representation. In some embodiments, next generation sequencing platform (e.g., those described herein) specific adapters are incorporated into ROI amplicons either during the initial amplicon generation reaction or during a separate post amplicon generation step (e.g. ligation).

In some embodiments, the amplicon based NGS libraries are then sequenced (e.g., using a NGS method) and the data output is used to determine relative copy number status of the ROI. In some embodiments, an altered copy number (e.g., increase or decrease (e.g., due to genomic deletions)) is observed based on an altered (e.g., increased or decreased) number of reads compared to the control. In some embodiments, copy number ratios are altered by a factor of 2 or more (e.g., 3 or more, 5 or more, 10 or more, 20 or more, or 40 or more). The copy number variation observed depends on the region of interest.

In some embodiments, amplicons are generated to the gene known to have copy number alterations in some individuals/tumor types as well as to control regions either on the same chromosome as the gene being interrogated for copy number variation or to a control region on a different nucleic acid (e.g., chromosome).

In some embodiments, assays detect known copy number variations that have clinical relevance. For example, EGFR copy number amplification has been shown to be present in glioblastoma samples but not control samples. FIGS. 3-6 show the theoretical results of analysis methods of embodiments of the present disclosure using a variety of copy number changes and amounts of tumor cells in a sample. The figures show that depending on the copy number change and the level of tumor cells in a sample, the sensitivity of the assay can vary.

In some embodiments, the region of interest is a region of genomic DNA corresponding to one or more genes or loci or chromosomes.

Figure 9:
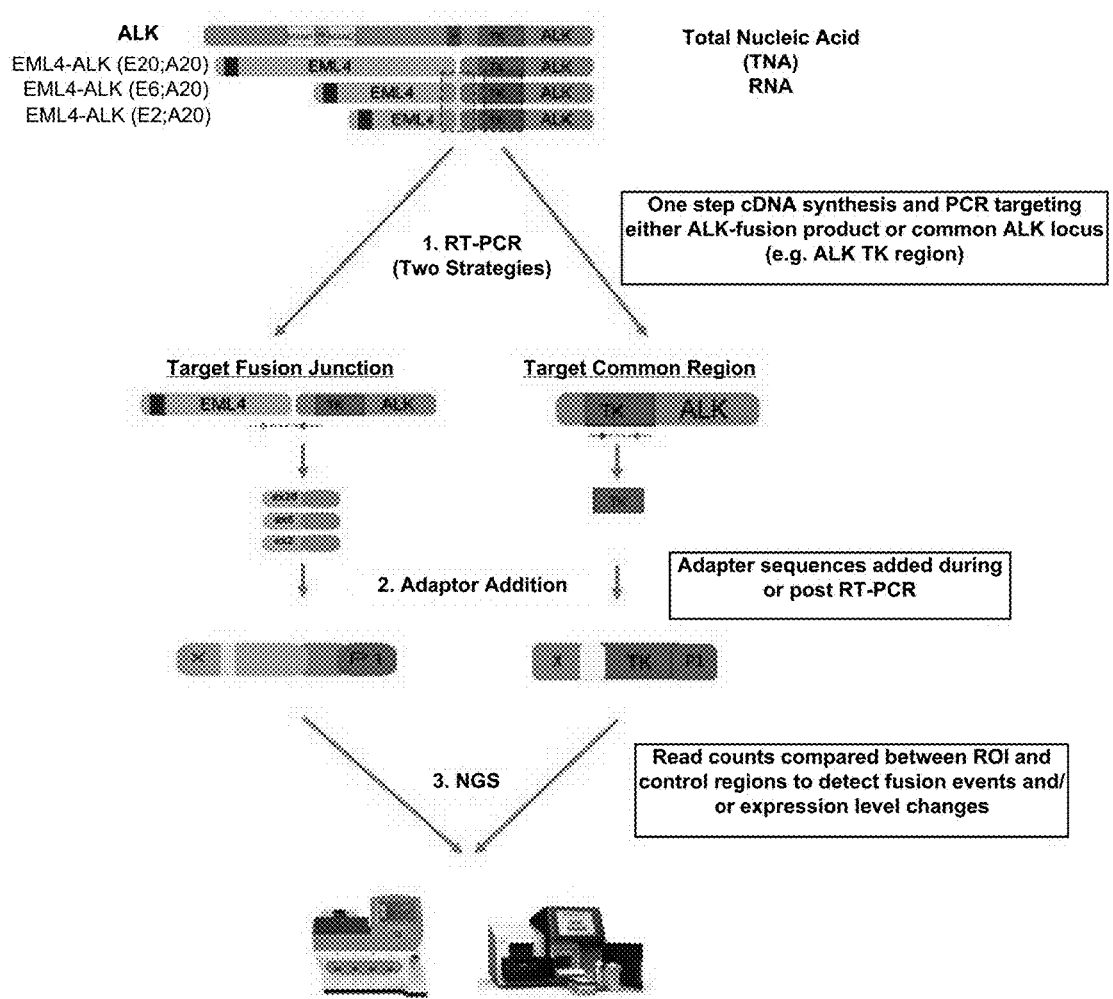
FIG. 9 shows detection of gene fusions and/or expression level changes using methods of embodiments of the present disclosure.

In some embodiments, the region of interest is mRNA expressed from a gene of interest. In some embodiments, expression of a gene or region of interest is altered due to a gene fusion (See e.g., FIG. 9). Gene fusions are present in a variety of cancers and can result in increased or decreased levels of expression of a gene or expression of a gene not normally expressed. Examples of gene fusions associated with cancer are described, for example, in U.S. Pat. No. 7,718,369 and U.S. Patent Publications 2011-0028336 and 2012-0015839, each of which is herein incorporated by reference in its entirety.

a. Amplification and Anchor Incorporation

In some embodiments, regions of interest, along with control regions, are amplified prior to sequencing. In some embodiments, a control on the same chromosome as the region of interest is included. In some embodiments, a second control on a different chromosome is included. For example, a control located in the same chromosome is used for normalization for locus specific amplification. A second control located on a different nucleic acid (e.g., of known copy number) (e.g., a plasmid, mitochondrial DNA, synthetic DNA, or a different chromosome) is used to normalize copy number or gene expression. In some embodiments, the ratio of nucleic acid of control 1 to control 2 is compared to the ratio of nucleic acid from the region of interest to control 2. An increase in the amount of nucleic acid from the region of interest compared to control 2 relative to the amount of nucleic acid of control 1 compared to control 2 is indicative of genomic amplification of the region of interest (e.g., C1/C2 vs. ROI/C2), while a decrease is indicative of a copy number decrease or deletion.

In some embodiments, one or more controls are chosen for which the copy number is known. In some embodiments, multiple controls are utilized and the number of reads is averaged or the mean of the number of reads is utilized. In some embodiments, the controls are optimized for the particular region of interest to be detected. For example, in some embodiments a control that is not amplified in one type of cancer may be amplified in another and is thus not a preferred control in the cancer in which it is amplified.

The present invention is not limited to a particular type of primer. Examples include, but are not limited to, chemically modified primers, fluorescence-modified primers, functional primers (fusion primers), sequence specific primers, random primers, primers that have both specific and random sequences, and DNA and RNA primers.

In some embodiments, anchors for NGS sequencing are added during amplification or after amplification. In some embodiments, anchors are ligated to amplicons after amplification. In some embodiments, anchors are utilized to sequence regions of interest. Exemplary anchors specific for the sequencing technology are utilized and vary depending on the sequencing technology selected.

In some embodiments, low cycle PCR is used to maintain copy number representation. For example, in some embodiments, 45 or fewer (e.g., 45, 40, 35, 34, 33, 32, 31, 30, 29, 28, 27, 26, 25, 24, 23, 22, 20, 15, 10 or fewer) cycles of amplification are performed.

Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and U.S. Pat. No. 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPs to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applica-*

*tions* (Persing et al., Eds.), pp. 51-87 (American Society for Microbiology, Washington, D.C. (1993)).

In some embodiments, amplification is isothermal amplification method. In some embodiments, amplification methods are solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule are used. In some embodiments, methods that rely on bridge PCR, where both PCR primers are attached to a surface (see, e.g., WO 2000/018957, U.S. Pat. No. 7,972,820; U.S. Pat. No. 7,790,418 and Adessi et al., Nucleic Acids Research (2000): 28(20): E87; each of which are herein incorporated by reference) are used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

Examples of nucleic acid polymerases suitable for use in embodiments of the present invention include, but are not limited to, DNA polymerase (Klenow fragment, T4 DNA polymerase), thermostable DNA polymerases (Perler F. B. et al., Adv. Protein Chem. 1996, 48:377-435) identified and cloned in a variety of thermostable bacteria (such as Taq, VENT, Pfu, Tfl DNA polymerases) as well as their genetically modified derivatives (TaqGold, VENTexo, Pfu exo). Preferably the nucleic acid polymerase used for colony primer extension is stable under temperature at which the primer and template hybridization results enough specific to avoid incomplete or spurious amplifications of the template.

The amplification solution contains preferably, deoxyribonucleoside triphosphates, for example dATP, dTTP, dCTP, dGTP, naturally or non-naturally occurring, for example modified with a fluorescent or radioactive group. A large variety of synthetically modified nucleic acids have been developed for chemical and biological methods in order to increase the detectability and/or the functional diversity of nucleic acids. These functionalized/modified molecules (e.g., nucleotide analogs) can be fully compatible with natural polymerizing enzymes, maintaining the base pairing and replication properties of the natural counterparts, as recently reviewed (Thum O et al., Angew. Chem. Int. Ed. 2001, 40 (21): 3990-3993).

Other components of the amplification solution are added consequently to the choice of the nucleic acid polymerase, and they are essentially corresponding to compounds known in the art as being effective to support the activity of each polymerase. The concentration of compounds like dimethyl sulfoxide (DMSO), Bovine Serum Albumin (BSA), polyethylene glycol (PEG), Betaine, Triton X-100, or $MgCl_2$ is well known in the prior art as being important to have an optimal amplification, and therefore the operator can easily adjust such concentrations for the methods of the present invention on the basis of the examples presented hereafter.

B. Sequencing

In some embodiments, nucleic acid sequencing methods are utilized for detection. In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, detection methods utilize hybridization assays. Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; inkjet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

C. Analysis

In some embodiments, a computer-based analysis program is used to translate the raw data generated by the detection assay (e.g., sequencing reads) into data of predictive value for an end user (e.g., medical personnel). The user can access the predictive data using any suitable means. Thus, in some preferred embodiments, the present invention provides the further benefit that the user, who is not likely to be trained in genetics or molecular biology, need not understand the raw data. The data is presented directly to the end user in its most useful form. The user is then able to immediately utilize the information in order to determine useful information (e.g., in medical diagnostics, research, or screening).

The present invention contemplates any method capable of receiving, processing, and transmitting the information to and from laboratories conducting the assays, information provides, medical personal, and subjects. For example, in some embodiments of the present invention, a sample (e.g., blood, cell or tissue sample) is obtained from a subject and submitted to a profiling service (e.g., lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a cheek swab) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., sequencing data), specific for the information desired for the subject. The data is then prepared in a format suitable for interpretation by the end user (e.g., medical personnel). For example, rather than providing raw data, the prepared format may represent a conclusion or assessment (e.g., presence of disease, risk of disease developing, likelihood of disease being present, or prognosis of disease) for the subject. The data may be displayed to the user by any suitable method. For example, in some embodiments, the profiling service generates a report that can be printed for the user or displayed on a computer monitor.

In some embodiments, the information is first analyzed at a local medical facility or at a regional facility. The raw data is then sent to a central processing facility for further analysis and/or to convert the raw data to information useful for the user. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the end user, the subject, or researchers.

D. Systems and Kits

In some embodiments, the present invention provides kits and systems for the amplification and/or analysis of nucleic acids. In some embodiments, kits include reagents necessary, sufficient or useful for analysis and detection of copy number or gene expression changes (e.g., primers, probes, anchors, solid supports, reagents, controls, instructions, etc.). For example, in some embodiments, kits comprise primers and anchors for amplification and sequencing of regions of interest and control regions. In some embodiments, kits include analysis software (e.g., to analyze sequencing data).

In some embodiments, kits comprise one or more containers that comprise reagents, primers, probes, anchors, solid supports, buffers, and the like. In some embodiments, each component of the kit is packaged in a separate container. In some embodiments, the containers are packed and/or shipped in the same kit or box for use together. In some embodiments, one or more components of the kit are shipped and/or packaged separately.

In some embodiments, systems include automated sample and reagent handling devices (e.g., robotics).

II. Uses

The systems and methods described herein find use in a variety of research, screening, and diagnostic applications. In some embodiments, amplification and sequencing methods described herein find use in the diagnosis, prognosis, and screening of disease (e.g., cancer). In some embodiments, the systems and methods described herein are utilized for predicting a predisposition to a disease in a subject, diagnosing a disease in a subject, predicting the likelihood of recurrence of disease in a subject, providing a prognosis for a subject with a disease, or selecting a subject with a disease for treatment with a particular therapy. These processes preferably comprise providing a genomic DNA or mRNA sample from a subject; and detecting the amplification of a gene or increased expression of a gene by the processes described above. In some embodiments, an increased copy number or increased expression of a regions of interest is indicative of a predisposition of the subject to a disease, an indication that the subject has a disease, an indication of the likelihood of recurrence of a disease in the subject, an indication of survival of the subject, and an indication that the subject is a candidate for treatment with a particular therapy.

For example, in some embodiments, the results of altered chromosomal copy number or gene expression or the level of altered chromosomal copy number or gene expression changes observed are indicative of the presence, absence, or prognosis of a disease (e.g., cancer). In some embodiments, altered chromosomal copy number or gene expression is used to determine a treatment course of action (e.g., the choice of drug therapy regimen). In some embodiments, altered chromosomal copy number or gene expression is used to determine a prognosis (e.g., aggressiveness of disease, likelihood of disease to spread, or likelihood of disease to recur). In some embodiments, the prognosis is used to determine a treatment course of action. In some embodiments, the degree of copy number or gene expression changes observed vary based on disease severity or prognosis and can be used to determine a prognosis or treatment course of action.

In some embodiments, the disease is cancer. For example, copy number amplification of the EGFR locus is associated with glioblastoma and non-small cell lung cancer (Cappuzzo F, Hirsch, et al. (2005) Journal of the National Cancer Institute 97 (9): 643-655). In addition, a higher copy number of CCL3L1 has been associated with lower susceptibility to HIV infection (Gonzalez E, et al. (2005). "The Influence of CCL3L1 Gene-Containing Segmental Duplications on HIV-1/AIDS Susceptibility". Science 307 (5714): 1434-1440), and a low copy number of FCGR3B (the CD16 cell surface immunoglobulin receptor) can increase susceptibility to systemic lupus erythematosus and similar inflammatory autoimmune disorders (Aitman T J, et al. (2006) Nature 439 (7078): 851-855). Copy number variation has also been associated with autism (Cook E H, Scherer S W (2008) Nature 455 (7215): 919-23; Pinto J, et al. (2010) Nature 466 (7304): 368-72; Sebat J, et al. (2007) Science 316 (5823): 445-9; Gai X, et al. (2011) Mol Psychiatry 17 (4): 402-11), schizophrenia (Cook et al. supra; St Clair D (2008) Schizophr Bull 35 (1): 9-12) and idiopathic learning disability (Knight S, et al. (1999) The Lancet 354 (9191): 1676-81).

EXPERIMENTAL

The following examples serve to illustrate certain preferred embodiments and aspects of the present invention and are not to be construed as limiting the scope thereof.

Example 1

EGFR copy number amplification has been shown to be present in glioblastoma samples compared to control. The experiment described here was performed to determine if the Ion Torrent next generation sequencing platform can be used to detect EGFR copy number variation. FIGS. 1 and 2 show schematics of the assay design.

| Reagents and Kits: | |
| --- | --- |
| Component | Catalog # |
| Ion Plus Fragment Library Kit | 4471252 |
| Ampure XP Reagent | A63880 |
| Ion PGM 200 Sequencing Kit | 4474007 |
| Ion Xpress Barcode Adapters 1-16 Kit | 4471250 |
| Ion Library TagMan Quantitation Kit | 4468802 |
| Ion OneTouch 200 Reagents Kit v2 | 4478316 |
| Dynabeads MyOne Streptavidin C1 | 650.01 |
| Ion Sphere Quality Control Kit | 4468656 |
| Ion PGM 314 Chip | 800-3140-01 |
| Bioanalyzer High Sensitivity DNA Reagent | 5067-4626 |
| gDNA sample 1167348B 54.1 ng/uL | N/A |
| gDNA sample 1167356B 67.2 ng/uL | N/A |
| Chr1_1E8b1f (primer) | N/A |
| Chr1_1E8b1r (primer) | N/A |
| Chr1-1E8b1p (probe) | N/A |
| EGFRint7f (primer) | N/A |
| EGFRex8r (primer) | N/A |
| EGFRex8FAM (probe) | N/A |
| PCR Reagents - AmpliTaq Gold Enzyme | 33794 |
| PCR Reagents - 25 mM dNTP | 32343 |
| PCR Reagents - 2.5 uM ROX | 251420 |
| PCR Reagents - 1M Tris-HCl 59311 | 22200001 |
| PCR Reagents - 10X CT/NG Oligo Buffer | 36774 |
| PCR Reagents - MgCl2 | M1028- 100 ML |
| Molecular Biology Grade Water | 55451 |

Instruments

| Instrument | Instrument Name |
|---|---|
| Ion Torrent PGM | PGM02 |
| Ion Torrent PGM | PGM01 |
| Ion Torrent OneTouch | 441 |
| Ion Torrent OneTouch | 445 |
| Ion Torrent Enrichment Station | 1884 |
| Ion Torrent Enrichment Station | 1886 |
| Bioanalyzer 2100 | Bioanalyzer |

Software

| Software Name | Version |
|---|---|
| Ion Torrent PGM | version 2.2 |
| Ion OneTouch | version 37 |
| Ion Torrent Suite | version 2.2 |
| CLC Genomics Workbench | version 5.5 |

Real time PCR was performed on the M2000RT (Abbott Molecular, Abbott Park, Ill.) with 20 ng of control sample and EGFR amplified sample to select the total number of cycles used to generate amplicons for Ion Torrent next generation sequencing library production. A low number of PCR cycles was used to maintain copy number representation.

PCR Set Up:

|  |  | MgCl2 | dNTP | TaqGold | ROX |
|---|---|---|---|---|---|
|  |  | 7 | 0.8 | 6 | 5x |

| | | | | Fold [ ] | | | | |
|---|---|---|---|---|---|---|---|---|
| # of reactions | 2.5 | | | | | | | |
| Total Volume/RXN | 50 | | | | | | | |
| Volume of Component Mix | 49 | | | | | | | |
| Reagent | Lot | Stock | Units | 1.0204 | units | 1X Vol | unit | RXN | unit |
| EGFRint7f | | 100 | uM | 0.5102 | uM | 0.6 | uL | 0.5 | uM |
| EGFRex8r | | 100 | uM | 0.5102 | uM | 0.6 | uL | 0.5 | uM |
| EGFRex8FAM | | 50 | uM | 0.2041 | uM | 0.5 | uL | 0.2 | uM |
| ROX | | 2.5 | uM | 0.0612 | uM | 3.0 | uL | 0.06 | uM |
| Chr1_1E8b1f | | 100 | uM | 0.5102 | uM | 0.6 | uL | 0.5 | uM |
| Chr1_1E8B1r | | 100 | uM | 0.5102 | uM | 0.6 | uL | 0.5 | uM |
| Chr1_1E8b1P | | 50 | uM | 0.2041 | uM | 0.5 | uL | 0.2 | uM |
| 10 CT/NG Oligo Buffer | | 10 | X | 0.5102 | X | 6.3 | uL | 0.5 | x |
| 1M Tris-HCl 59311 | | 66.667 | X | 3.5714 | X | 6.6 | uL | 3.5 | x |
| MgCl2 | | 1 | M | 0.0071 | M | 0.9 | uL | 0.007 | M |
| dNTP | | 25 | mM | 0.8163 | mM | 4.0 | uL | 0.8 | mM |
| AmpliTaq Gold | | 5 | U/uL | 11 | U | 5.5 | uL | 11 | U/rxn |
| Molecular Biololgy Water | | | | | | 92.8 | uL | | |
| Final Volume | | | | | | 122.5 | uL | | |

Cycling:

| All Plates | Cycling |
|---|---|
| Ramping: Fast | Volume = 50 ul |
| Stage 1: 1 cycle: | Step 1: 94.0 C. for 10 minutes |
| Stage 2: 4 cycles | Step 1: 92.0 C. for 30 seconds |
| | Step 2: 60 C. for 30 seconds (1 sec auto-increment) |
| Stage 3: 50 cycles | Step 1: 92.0 C. for 30 seconds |
| | Step 2: 60 C. for 30 seconds (1 sec auto-increment) |
| | Step 3: 58.0 C. for 40 seconds (read) |

Plate Configuration:

| | 1 | 2 |
|---|---|---|
| A | | |
| B | | |
| C | | |
| D | | 356BR sample |
| E | | 348BR sample | qPCR Results:

Probes were read during Stage 3, the 50 cycle stage. Prior to Stage 3, four cycles were performed in Stage 2. Based on the real time results, 27 total cycles was selected for amplicon production for NGS CNV library preparation.

The same PCR set up as in step 1 above was performed but only for 27 total cycles (stage 2=4 cycles; stage 3=23 cycles). Probes were not included in this PCR as these amplicons would go on to Ion Torrent adapter ligation.

| Reagent | Original Stock | Units | Original volume | Units | New Stock | Units | New volume | Units | Water Added to Original volume | units |
|---|---|---|---|---|---|---|---|---|---|---|
| non-amp (356BR) | 67.2 | ng/uL | 7.4 | uL | 20 | ng/uL | 24.864 | uL | 17.464 | uL |
| amp (348BR) | 54.1 | ng/uL | 9.2 | uL | 20 | ng/uL | 24.886 | uL | 15.686 | uL |
| EGFRex8FAM | 217.64 | uM | 50 | uL | 50 | uM | 217.64 | uL | 167.64 | uL |
| Chr1_1E8b1P | 317.79 | uM | 50 | uL | 50 | uM | 317.79 | uL | 267.79 | uL |

3 reactions=20 ng of 356BR ('not EGFR amplified' sample)
3 reactions=20 ng of 348BR ('EGFR amplified' sample)
Master Mix:

|  |  | MgCl2 | dNTP | TaqGold | ROX |  |  |  |  |
|  |  | 7 | 0.8 | 6 | 5x |  |  |  |  |
| # of reactions | 7.5 |  |  |  |  |  |  |  |  |
| Total Volume/RXN | 50 |  |  |  |  |  |  |  |  |
| Volume of Component Mix | 49 |  |  | Fold [ ] |  |  |  |  |  |
| Reagent | Lot | Stock | Units | 1.0204 | units | 1X Vol | unit | RXN | unit |
| EGFRint7f |  | 100 | uM | 0.5102 | uM | 1.9 | uL | 0.5 | uM |
| EGFRex8r |  | 100 | uM | 0.5102 | uM | 1.9 | uL | 0.5 | uM |
| EGFRex8FAM |  | 50 | uM | 0.2041 | uM | 0.0 | uL | 0.0 | uM |
| ROX |  | 2.5 | uM | 0.0612 | uM | 0.0 | uL | 0.0 | uM |
| Chr1_1E8b1f |  | 100 | uM | 0.5102 | uM | 1.9 | uL | 0.5 | uM |
| Chr1_1E8B1r |  | 100 | uM | 0.5102 | uM | 1.9 | uL | 0.5 | uM |
| Chr1_1E8b1P |  | 50 | uM | 0.2041 | uM | 0.0 | uL | 0.0 | uM |
| 10 CT/NG Oligo Buffer |  | 10 | X | 0.5102 | X | 18.8 | uL | 0.5 | x |
| 1M Tris-HCl 59311 |  | 66.667 | X | 3.5714 | X | 19.7 | uL | 3.5 | x |
| MgCl2 |  | 1 | M | 0.0071 | M | 2.6 | uL | 0.007 | M |
| dNTP |  | 25 | mM | 0.8163 | mM | 12.0 | uL | 0.8 | mM |
| AmpliTaq Gold |  | 5 | U/uL | 11 | U | 16.5 | uL | 11 | U/rxn |
| Molecular Biololgy Water |  |  |  |  |  | 290.4 | uL |  |  |
| Final Volume |  |  |  |  |  | 367.5 | uL |  |  |

Cycling:

| All Plates | Cycling |
| --- | --- |
| Ramping: Fast | Volume = 50 ul |
| Stage 1: 1 cycle: | Step 1: 94.0 C. for 10 minutes |
| Stage 2: 4 cycles | Step 1: 92.0 C. for 30 seconds |
|  | Step 2: 60 C. for 30 seconds (1 sec auto-increment) |
| Stage 3: 23 cycles | Step 1: 92.0 C. for 30 seconds |
|  | Step 2: 62.0 C. for 30 seconds (1 sec auto-increment) |
|  | Step 3: 58.0 C. for 40 seconds (read) |

Plate Configuration:

|  | 1 | 2 | 3 | 4 |
| --- | --- | --- | --- | --- |
| A |  |  |  |  |
| B |  |  |  |  |
| C |  |  |  |  |
| D |  | 356BR sample | 356BR sample | 356BR sample |
| E |  | 348BR sample | 348BR sample | 348BR sample |
| F |  |  |  |  |
| G |  |  |  |  |
| H |  |  |  |  |

After PCR amplification, amplicon libraries were prepared Ion Torrent's 'Short Amplicon (<250 bp) Library Preparation' protocol. Because the amount of amplicons produced should differ significantly between the EGFR non-amplified and amplified samples, several adjustments were made to the Ion Torrent library preparation protocol. These protocol changes are listed below.

After 27 cycles of PCR, amplicons were cleaned up with Ampure XP beads (1:1.8; v/v; sample:Ampure XP reagent)
 90 uL of Ampure XP reagent added
  Ampure XP bead washes performed with 30 uL of 70% ethanol
  15 uL of Nuclease free water was added to resuspend the dried Ampure XP beads
  14 uL of the supernatant was collected (Ampure XP purified amplicon sample) End Repair For end repair the three like samples were pooled so that a total of two tubes were taken through End Repair (one 356BR tube and one 348BR tube)

End Repair Set up:
 14 uL×3=42 uL purified amplicon
 195 uL of nuclease free water
 60 uL of 5× End Repair Buffer (Ion Plus Fragment Library Kit)
 3 uL End Repair Enzyme (Ion Plus Fragment Library Kit)
TOTAL: 300 uL
 20 minutes room temperature
7. End Repair Ampure XP Bead Clean-Up
 Added 540 uL of AmpureXP reagent to each tube, mixed, pulse-spin, 5 minutes room temperature
 Promega Magnetic Rack 3 minutes
 Removed supernatant (unbound)
 Performed two ethanol washes with 500 uL 70% ethanol
 Air dried beads for 5 minutes at room temperature
 Resuspended beads with 75 uL of Low TE
 Placed sample on Promega Magnetic Rack for 3 minutes
 Collected the supernatant from each
Ligate Adapters, Nick Repair, and Purify
 For each sample three adapter concentrations were tested: 0.2× adapters, 1× adapters, and 5× adapters.
 For each sample, 24 uL of sample pool from the previous step was used
 Ligation Set up

| Ion Torrent Ligation Set up | | | |
| --- | --- | --- | --- |
| | Reaction | | |
| Component | 0.2X Adapter Condition Volume (uL) | 1X Adapter Condition Volume (uL) | 5X Adapter Condition Volume (uL) |
| DNA | 24 | 24 | 24 |
| 10X Ligase Buffer | 10 | 10 | 10 |
| Ion P1 Adapter | 2 (1:5 diluted adapter) | 2 | 10 |
| Ion Xpress Barcode X | 2 (1:5 diluted adapter) | 2 | 10 |

| Ion Torrent Ligation Set up | | | |
|---|---|---|---|
| dNTP Mix | 2 | 2 | 2 |
| Nuclease free water | 50 | 50 | 34 |
| DNA Ligase | 2 | 2 | 2 |
| Nick Repair Polymerase | 8 | 8 | 8 |
| Total | 100 | 100 | 100 |

| Library Barcode | |
|---|---|
| Sample | |
| Ion Xpress Barcode 001 | 356BR (non-amplified) |
| Ion Xpress Barcode 003 | 348BR (amplified) |

| Ligation Time/Temperature | | |
|---|---|---|
| Stage | Temperature | Time |
| Hold | 25° C. | 15 minutes |
| Hold | 72° C. | 5 minutes |
| Hold | 4° C. | infinite |

After Ligation Reaction Transferred to a 1.5-mL LoBind Tube for Cleanup
  Ampure XP beads used for cleanup at 1:1.8 ratio; 180 uL of Ampure XP reagent added to each 100 uL ligation reaction.
  Ampure XP bead protocol performed as listed on page 15 in Ion preparing short amplicon library preparation protocol.
  19 uL of final cleaned up product collected for each library (6 libraries at this point; 3 not EGFR amplified that used either a 0.2×, 1×, or 5× adapter concentration and 3'EGFR amplified) that used either a 0.2×, 1×, or 5× adapter concentration.
Libraries were run on an Agilent Bioanalyzer High Sensitivity DNA chip.
  Because adapter peaks were present on the Bioanalyzer output an additional 1:1.6 v:v (sample:Ampure XP reagent) was performed on each library (19 uL library: 30.4 uL Ampure XP reagent).
  Because partial adapter incorporation was present on the Bioanalyzer output for the 0.2× adapter libraries, only the 1× and 5× adapter libraries were continued.
The concentration of each library was determined using Ion Torrent's 'Ion Library Quantitation Kit' The template dilution factor from Ion's Quantitation Kit was used to load libraries onto OneTouch for emulsion PCR.

Ion Library Quantitation qPCR Set Up:

Number of reactions 36
Reaction Volume 25 uL
Master Mix

| | Each rxn | MM Vol | unit |
|---|---|---|---|
| Ion library TaqMan qPCR Mix, 2X | 12.5 | 450.0 | uL |
| Ion Library Taqman Quantitation Assay, 20X | 1.25 | 45.0 | uL |
| Nuclease-free water | 5 | 180.0 | uL |
| | 18.75 | 675.0 | |
| calc # rxns supported | | 36.0 | |
| Add 18.75 uL of master mix to each reaction | | | |
| Add 6.25 uL of Target | 6.25 | 225 | |
| total volume each rxn | 25 | 900.0 | |
| total calculated vol of each rxn | 25 | | |

| E. coli | | | |
|---|---|---|---|
| Standard Dilutions | | | |
| Standard | Control Library | Water | Fold dilution |
| 1 | 5 μL (undiluted) | 45 μL | 0.1 |
| 2 | 5 μL Std 1 | 45 μL | 0.01 |
| 3 | 5 μL Std 2 | 45 μL | 0.001 |
| 4 | 5 μL Std 3 | 45 μL | 0.0001 |
| 5 | 5 μL Std 4 | 45 μL | 0.00001 |

| Library Dilutions | | | | | |
|---|---|---|---|---|---|
| Dilution | Dilution alt name | Library (uL) | Library Dilution Used | Water (uL) | Total (uL) |
| 0.05 | 1:20 | 1 | 1.0000 | 19 | 20 |
| 0.001 | 1:1000 | 2 | 0.0500 | 98 | 100 |
| 0.0001 | 1:10K | 5 | 0.0010 | 45 | 50 |
| 0.000005 | 1:200K | 2.5 | 0.0001 | 47.5 | 50 |

| | 1 | 2 | 3 | 4 | 5 | 6 | 7 | 8 | 9 | 10 |
|---|---|---|---|---|---|---|---|---|---|---|
| A | E. coli 0.1 (6.8 pM) | | | | normal EGFR- 1: 1000 1:1 sample adapter | normal EGFR- 1: 1000 1:1 sample adapter | normal EGFR- 1: 10K 1:1 sample adapter | normal EGFR- 1: 10K 1:1 sample adapter | normal EGFR- 1: 200K 1:1 sample adapter | normal EGFR- 1: 200K 1:1 sample adapter |
| B | E. coli 0.01 (0.68 pM) | | | | normal EGFR- 1: 1000 5X adapter | normal EGFR- 1: 1000 5X adapter | normal EGFR- 1: 10K 5X adapter | normal EGFR- 1: 10K 5X adapter | normal EGFR- 1: 200K 5X adapter | normal EGFR- 1: 200K 5X adapter |
| C | E. coli 0.001 (0.068 pM) | | | | | | | | | |
| D | E. coli 0.0001 (0.0068 pM) | | | | | | | | | |
| E | E. coli 0.00001 (0.00068 pM) | | | | GBM- EGFR- 1: 1000 1:1 sample adapter | GBM- EGFR- 1: 1000 1:1 sample adapter | GBM- EGFR- 1: 10K 1:1 sample adapter | GBM- EGFR- 1: 10K 1:1 sample adapter | GBM- EGFR- 1: 200K 1:1 sample adapter | GBM- EGFR- 1: 200K 1:1 sample adapter |

|   | 1 | 2 | 3 | 4 | 5 | 6 | 7 | 8 | 9 | 10 |
|---|---|---|---|---|---|---|---|---|---|---|
| F |   |   |   |   | GBM-EGFR-1: 1000 5X adapter | GBM-EGFR-1: 1000 5X adapter | GBM-EGFR-1: 10K 5X adapter | GBM-EGFR-1: 10K 5X adapter | GBM-EGFR-1: 200K 5X adapter | GBM-EGFR-1: 200K 5X adapter |
| G |   |   |   |   |   |   |   |   |   |   |
| H | NC | NC |   |   |   |   |   |   |   |   |

Summary of Ion Library Quantitation Results:

| library name | qPCR relative quantity | Sample Library fold Dilution | TDF | Mean TDF |
|---|---|---|---|---|
| 348BR-1:1,000 1:1 sample:adapter | 0.17 | 1000 | 527.25 | 567.38 |
| 348BR-1:10,000 1:1 sample:adapter | 0.02 | 10000 | 572.24 |   |
| 348BR-1:200,000 1:1 sample:adapter | 0.00 | 200000 | 562.53 |   |
| 348BR-1:1,000 5X adapter | 0.09 | 1000 | 287.52 | 278.74 |
| 348BR-1:10,000 5X adapter | 0.01 | 10000 | 277.84 |   |
| 348BR-1:200,000 5X adapter | 0.00 | 200000 | 280.43 |   |
| 356BR-1:1,000 1:1 sample:adapter | 0.02 | 1000 | 52.52 | 49.97 |
| 356BR-1:10,000 1:1 sample:adapter | 0.00 | 10000 | 49.57 |   |
| 356BR-1:200,000 1:1 sample:adapter | 0.00 | 200000 | 50.37 |   |
| 356BR-1:1000 5X adapter | 0.03 | 1000 | 96.93 | 86.55 |
| 356BR-1:10000 5X adapter | 0.00 | 10000 | 90.02 |   |
| 356BR-1:200000 5X adapter | 0.00 | 200000 | 83.09 |   |

| Estimated Final Library Stock Mean (pM) | Library |
|---|---|
| 12348.3 | 348BR 1X adapter |
| 6066.3 | 348BR 5X adapter |
| 1087.5 | 356BR 1X adapter |
| 1883.7 | 356BR 5X adapter |

Emulsion PCR (OneTouch) and bead enrichment (Enrichment Station (ES)) were performed. The Ion OneTouch 200 Template Kit v2 protocol was followed.

The template dilution factors from the 'Ion Library Quantitation Kit was used to dilute libraries prior to loading on the OneTouch. After diluting each library using the template dilution factor, 10 uL of each 1× adapter library were combined (total 20 uL) prior to loading on the OneTouch instrument. After diluting each library using the template dilution factor, 10 uL of each 5× adapter library were combined (total 20 uL) prior to loading on the OneTouch instrument.

The Ion Sphere Quality Control Kit was used to measure the quality of unenriched and enriched Ion Sphere Particles (ISPs).

The final product from each OneTouch/ES run was 100 uL of enriched Ion Sphere Particles (ISPs) in Ion OneTouch Wash Solution.'

PGM Sequencing was performed. The Ion PGM 200 Sequencing Kit Protocol was followed. Two PGM runs were performed. PGM02=two libraries. The following samples were run:

Ion Xpress Barcode 001='not EGFR amplified' that used 1× Ion adapter concentration during ligation.

Ion Xpress Barcode 003='EGFR amplified' that used 1× Ion adapter concentration during ligation.

PGM01=Two Libraries

Ion Xpress Barcode 001='not EGFR amplified' that used 5× Ion adapter concentration during ligation.

Ion Xpress Barcode 003='EGFR amplified' that used 5× Ion adapter concentration during ligation.

Results:

PGM Run Summary:

1. From Run#1, Instrument=PGM02, two libraries

Ion Xpress Barcode 001='not EGFR amplified' that used 1× Ion adapter concentration during ligation

|   | Count | Percentage |
|---|---|---|
| Total Addressable Wells | 1,262,531 |   |
| Wells with ISPs | 537,503 | 43% |
| Live ISPs | 388,263 | 72% |
| Test Fragment ISPs | 22,682 | 6% |
| Library ISPs | 365,581 | 94% |
| Library ISPs/Percent Enrichment | 365,581 | 71% |
| Filtered: Polyclonal | 92,337 | 25% |
| Filtered: Primer dimer | 116 | <1% |
| Filtered: Low quality | 84,782 | 23% |
| Final Library Reads | 188,346 | 52% |

Ion Xpress Barcode 003='EGFR amplified' that used 1× Ion adapter concentration during ligation Test Fragment Summary

| Test Fragment | Percent (50AQ17/Num) |
|---|---|
| TF_A | 94% |
| TF_D | 97% |

2. From Run#2, Instrument=PGM01, two libraries

Ion Xpress Barcode 001='not EGFR amplified' that used 5× Ion adapter concentration during ligation Ion Xpress Barcode 003='EGFR amplified' that used 5× Ion adapter concentration during ligation

|   | Count | Percentage |
|---|---|---|
| Total Addressable Wells | 1,262,519 |   |
| Wells with ISPs | 391,416 | 31% |
| Live ISPs | 322,647 | 82% |
| Test Fragment ISPs | 18,857 | 6% |
| Library ISPs | 303,790 | 94% |
| Library ISPs/Percent Enrichment | 303,790 | 82% |
| Filtered: Polyclonal | 88,424 | 29% |
| Filtered: Primer dimer | 64 | <1% |
| Filtered: Low quality | 101,743 | 33% |
| Final Library Reads | 113,559 | 37% |

Test Fragment Summary

| Test Fragment | Percent (50AQ17/Num) |
|---|---|
| TF_A | 92% |
| TF_D | 96% |

Ion Torrent Suite was used to generate library barcode demultiplexed. FASTQ files.

FASTQ files were imported into CLC Genomics Workbench

Read mapping was performed in CLC Genomics Workbench using the NGS Core Tools 'Map Reads to Reference Tool' using a reference containing the 104 bp EGFR Amplicon sequence and the 119 bp Chr1 region sequence.

Read counts after performing alignment per amplicon region are shown below

CNV Read Summary (CLC mapper)

| Library | Chr1 Amplicon Count | EGFR Amplicon Count | EGFR/Chr1 ratio (Within Library) | 384BR/356BR |
|---|---|---|---|---|
| 356BR_1X | 32430 | 36507 | 1.1 | 15.25700357 |
| 348BR_1X | 5952 | 102226 | 17.2 | |
| 356BR_5X | 24999 | 15997 | 0.6 | |
| 348BR_5X | 4763 | 59137 | 12.4 | 19.40272817 |

PGM Run Summary (CLC mapper)

| Library | total final # reads from PGM run | Chr1 Amplicon Count | Chr1 Amplicon % of total reads | EGFR Amplicon Count | EGFR Amplicon % of total reads | % reads mapping to Chr1 or EGFR | % reads mapping to Chr1 & EGFR from each sample |
|---|---|---|---|---|---|---|---|
| 356BR_1X | 188,346 | 32430 | 17% | 36507 | 19% | 94% | 37% |
| 348BR_1X | | 5952 | 3% | 102226 | 54% | | 57% |
| 356BR_5X | 113,559 | 24999 | 22% | 15997 | 14% | 92% | 36% |
| 348BR_5X | | 4763 | 4% | 59137 | 52% | | 56% |

Figure 7:
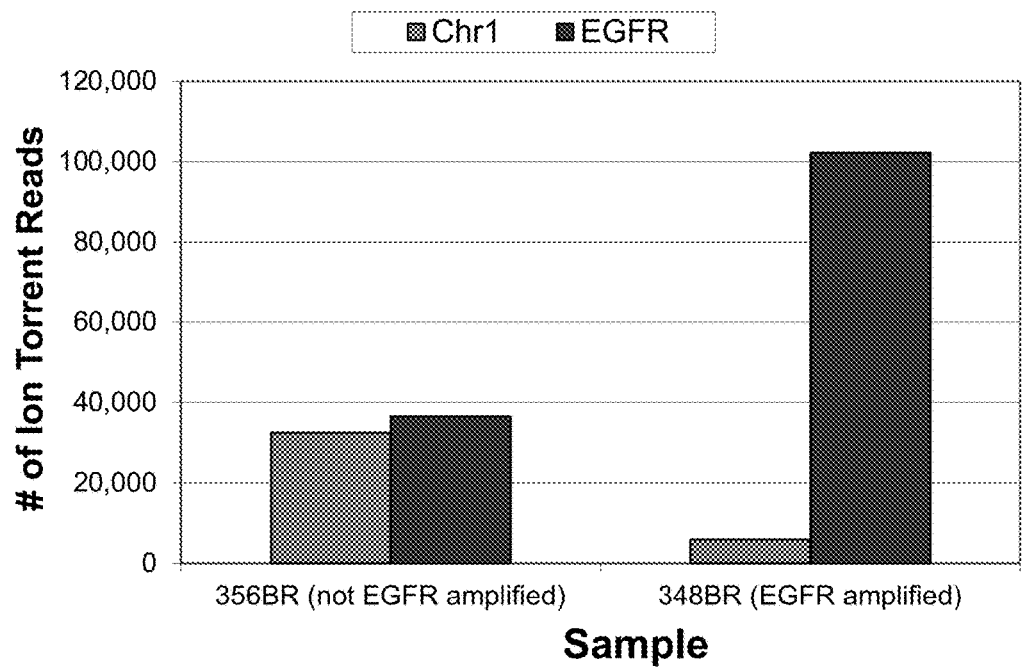
FIG. 7 shows detection of CNV of EGFR after sequencing using methods of embodiments of the present disclosure.
Figure 8:
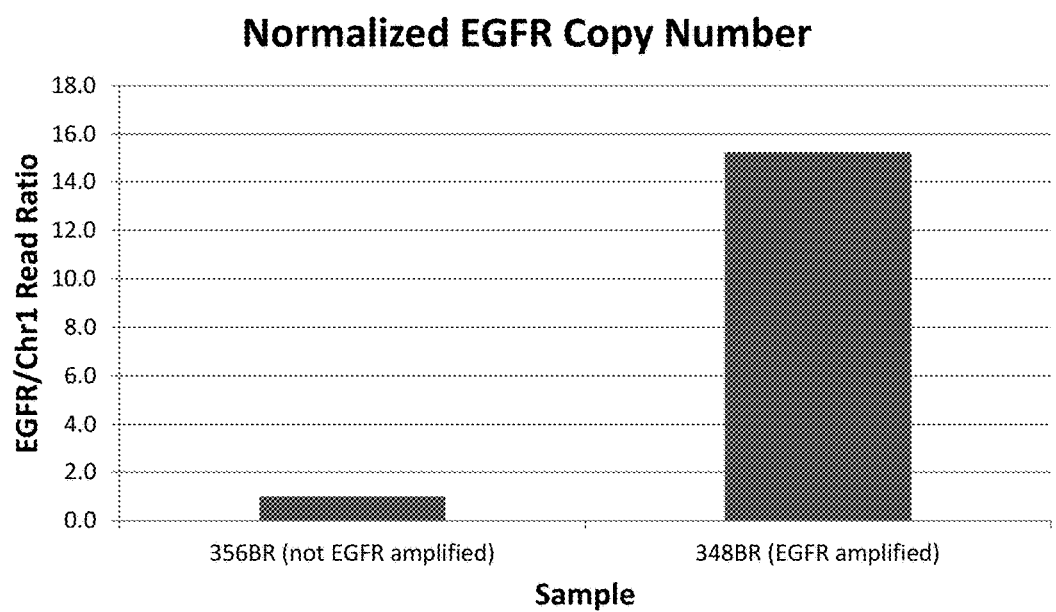
FIG. 8 shows detection of CNV of EGFR after sequencing using methods of embodiments of the present disclosure.

Conclusion: FIGS. 7-8 show detection of CNV of EGFR using the methods described above. The sample with known EGFR amplification (348BR) produced >10-fold more mapped reads compared to the EGFR non-amplified sample (356BR) in both library preparation conditions tested (1× Ion adapter concentration and 5× Ion adapter concentration). Next generation sequencing can be used to detect genomic copy number changes using a next generation sequencing library preparation protocol. Specifically, the Ion Torrent sequencer was able to detect genomic copy number changes.

Example 2

Multiplex Analysis

Figure 10:
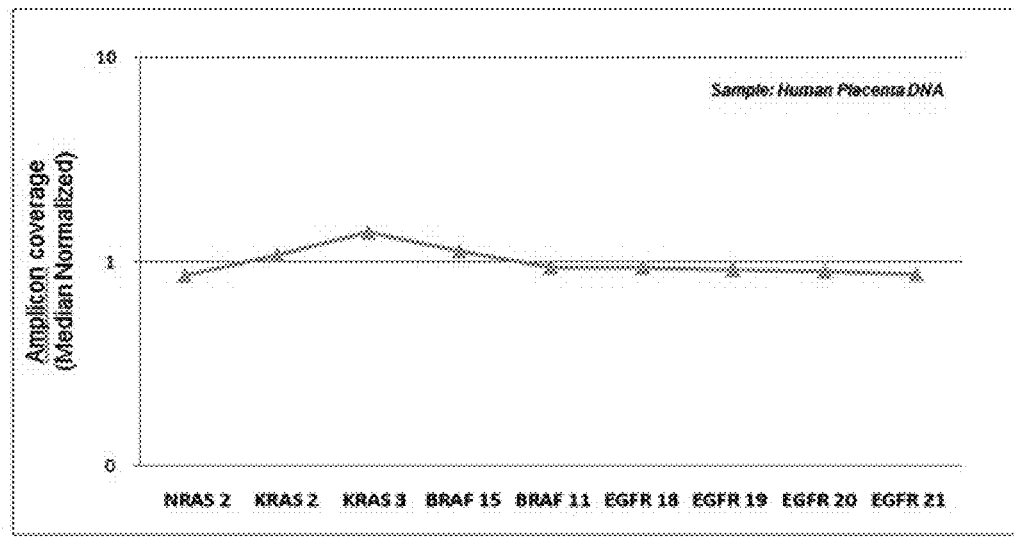
FIG. 10 shows results of multiplex PCR (9-plex) performed to generate amplicons covering EGFR (exons 18, 19, 20 and 21), KRAS (exons 2 and 3), BRAF (exons 11 and 15) and NRAS (exon 2).

Simultaneous interrogation of multiple regions of interest can be enabled by multiplex PCR. Amplicons covering the regions of interest can be generated and subsequently made compatible for sequencing. In sequence 'counting' applications, such as in copy number variation detection, having relatively equal amounts of amplicons generated during the initial PCR is important for downstream sequence analysis and determination of accurate and unambiguous copy number status of the regions of interests. FIG. 10 shows the result of the optimized multiplex PCR (9-plex) of nine different regions covering four different genes (EGFR, KRAS, BRAF and NRAS) and their relative coverage with each other determined by counting each of the amplicon sequences present using NGS.

FIG. 10 shows results of multiplex PCR (9-plex) performed to generate amplicons covering EGFR (exons 18, 19, 20 and 21), KRAS (exons 2 and 3), BRAF (exons 11 and 15) and NRAS (exon 2). These amplicon were used as input for NGS library generation and the resulting amplicon library was run on the Ion Torrent PGM. Each of the sequence (reads) were mapped to a reference sequence (hg19) and analyzed. Counts of each of the sequence corresponding to the nine targeted regions of interest above were tallied. Graph of the median-normalized amplicon sequence counts (coverage) among the nine targeted regions is shown. Human Placenta DNA was used input sample.

Figure 11:
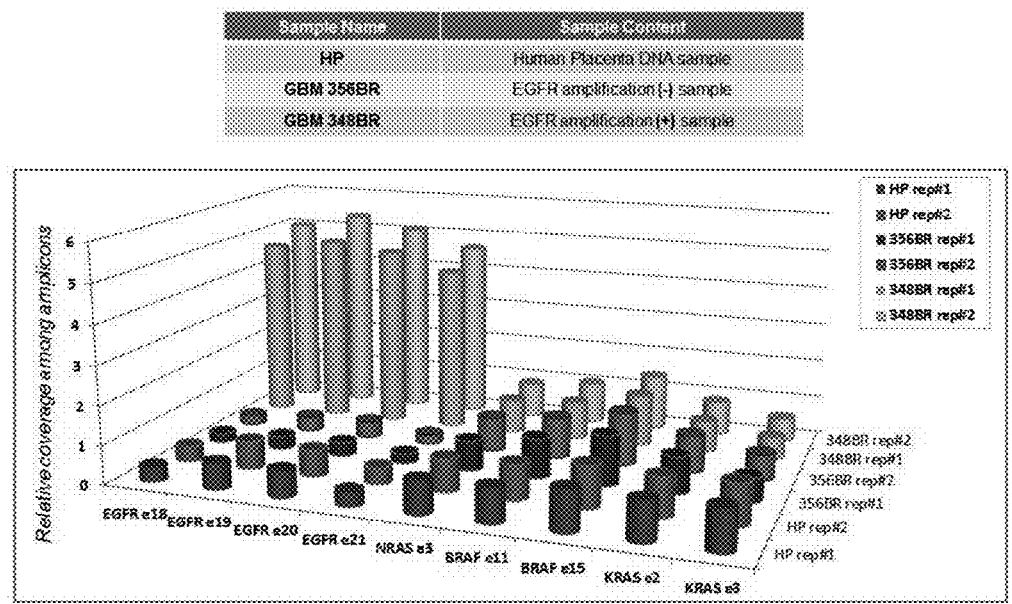
FIG. 11 shows copy number variation detection using multiplex PCR and NGS.

Once the 9-plex PCR was optimized and determined to produce relatively even amounts of the nine amplicons, the optimized multiplex PCR was performed using human placenta DNA [control 1, EGFR amplification (−)], Glioblastoma patient sample #356 [control 2, EGFR amplification (−)] and Glioblastoma patient sample #348BR [EGFR amplification (+)]. FIG. 11 below shows the relative amplicon coverage of each of the regions of interest and for the different samples. The EGFR amplicons for the sample #348BR have significantly increased coverage compared to other amplicons covering other genes, which is correlated to increased copy number of the EGFR gene in the sample. Both control samples, which do not have EGFR gene amplification, show relatively the same level of coverage compared to other amplicons corresponding to other regions of interest.

FIG. 11 shows copy number variation detection using multiplex PCR and NGS. Nine-plex PCR was performed to generate amplicons described above (FIG. 10) for a sample known to have EGFR gene amplification (Glioblastoma patient sample #348BR) along with two control samples (HP and Glioblastoma patient sample #356) known to not have EGFR gene amplification. Amplicon sequence analysis of the NGS data showed significant coverage increase for the amplicons covering EGFR compared to other amplicons for sample #348BR (EGFR amplification +), while the control samples had relatively even coverage for all the amplicons.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

sequencing; c) using said sequencing reads to compare the level of target amplicon to the level of control amplicon; and d) detecting chromosomal copy number changes or altered expression of said nucleic acid region of interest when the level of target amplicon is different than the level of at least one said control amplicon generated from said nucleic acid

---

---

We claim:

1. A method of detecting chromosomal copy number changes or altered expression of a nucleic acid region of interest, comprising: a) amplifying nucleic acid from said region of interest and at least one control region on the same chromosome as said region of interest and at least one control region on a different chromosome than said region of interest to generate a library of one or more target and one or more control amplicons; b) sequencing said target and control amplicons to generate sequencing reads wherein said sequencing is selected from the group consisting of pyrosequencing, sequencing-by-ligation, single molecule sequencing, sequence-by-synthesis (SBS), massive parallel clonal sequencing, massive parallel single molecule SBS, massive parallel single molecule real-time sequencing, and massive parallel single molecule real-time nanopore sequencing; c) using said sequencing reads to compare the level of target amplicon to the level of control amplicon; and d) detecting chromosomal copy number changes or altered expression of said nucleic acid region of interest when the level of target amplicon is different than the level of at least one said control amplicon generated from said at least one control region on the same chromosome as said region of interest.

2. The method of claim 1, wherein using said sequencing reads to compare the level of target amplicon to the level of control amplicon comprises comparing the ratio of the level of a first control amplicon to the level of a second control amplicon to the ratio of the level of said target amplicon to the level of said second control amplicon.

3. The method of claim 1, wherein said detected chromosomal copy number is altered by at least 2-fold.

4. The method of claim 1, wherein said detected chromosomal copy number is altered by at least 10-fold.

5. The method of claim 1, wherein said detected chromosomal copy number is altered by at least 20-fold.

6. The method of claim 1, wherein said amplifying comprises generating at least 2 amplicons from said region of interest.

7. The method of any claim 1, wherein said method further comprises the addition of nucleic acid adaptors to said amplicons during or after amplification.

8. The method of claim 1, wherein said amplifying comprises 45 or fewer cycles of amplification.

9. The method of claim 1, wherein said using said sequencing reads comprises base composition analysis.

10. The method of claim 1, comprising at least one control region comprising a plasmid, mitochondrial DNA, or synthetic DNA.

11. The method of claim 1, wherein said control sequencing reads are averaged.

12. The method of claim 1, comprising simultaneous amplification of a plurality of regions of interest using multiplex PCR.

* * * * *

UNITED STATES PATENT AND TRADEMARK OFFICE
CERTIFICATE OF CORRECTION

| | | |
|---|---|---|
| PATENT NO. | : 9,890,425 B2 | Page 1 of 1 |
| APPLICATION NO. | : 14/208874 | |
| DATED | : February 13, 2018 | |
| INVENTOR(S) | : Marc H. Domanus et al. | |

It is certified that error appears in the above-identified patent and that said Letters Patent is hereby corrected as shown below:

In the Claims

Column 1, Claim 7, Line 1 reads:
"7. The method of any claim 1, wherein said method further comprises the addition of nucleic acid adaptors to said amplicons during or after amplification."

Whereas it should read:
"7. The method of claim 1, wherein said method further comprises the addition of nucleic acid adaptors to said amplicons during or after amplification."

Signed and Sealed this
Fifth Day of June, 2018

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial
<220> FEATURE:
<223> OTHER INFORMATION: Synthetic

<400> SEQUENCE: 1
gtcatgcgtc cgagcctgtg ggg                                          23

<210> SEQ ID NO 2
<211> LENGTH: 23
<212> TYPE: DNA
<213> ORGANISM: Artificial
<220> FEATURE:
<223> OTHER INFORMATION: Synthetic

<400> SEQUENCE: 2
gtaatgcgtc cgagcctgtg ggg                                          23

<210> SEQ ID NO 3
<211> LENGTH: 26
<212> TYPE: DNA
<213> ORGANISM: Artificial
<220> FEATURE:
<223> OTHER INFORMATION: Synthetic

<400> SEQUENCE: 3
gtaattatgt ggtgacagat cacggc                                       26

<210> SEQ ID NO 4
<211> LENGTH: 26
<212> TYPE: DNA
<213> ORGANISM: Artificial
<220> FEATURE:
<223> OTHER INFORMATION: Synthetic

<400> SEQUENCE: 4
gtcattatgt ggtgacagat cacggc                                       26
```